United States Patent [19]
Wesson et al.

[11] 4,338,454
[45] Jul. 6, 1982

[54] PENTACHLOROPHENYL 3-(TRIETHOXYSILYL) PROPYL ETHER

[75] Inventors: John P. Wesson, Croton-on-Hudson, N.Y.; Thomas C. Williams, Ridgefield, Conn.; Robert G. Eagar, Jr., Yorktown Heights, N.Y.

[73] Assignee: Union Carbide Corporation, New York, N.Y.

[21] Appl. No.: 192,603

[22] Filed: Sep. 30, 1980

[51] Int. Cl.$^3$ .................................................. C07F 7/18
[52] U.S. Cl. ............................... 556/445; 106/15.05; 106/15.35; 106/287.34; 106/18.35
[58] Field of Search ........................................ 556/445

[56] References Cited

U.S. PATENT DOCUMENTS

| | | | |
|---|---|---|---|
| 2,783,262 | 2/1957 | Merker | 556/445 |
| 3,253,009 | 5/1966 | Allen et al. | 260/448.8 |
| 3,542,786 | 11/1970 | Weesner et al. | 260/279 |
| 3,657,305 | 4/1972 | Morehouse | 556/445 |
| 3,692,798 | 9/1972 | Barcza | 260/309 |
| 3,719,679 | 3/1973 | Michael et al. | 260/448.2 N |
| 3,860,709 | 1/1975 | Abbott et al. | 424/184 |

FOREIGN PATENT DOCUMENTS

| | | |
|---|---|---|
| 1010782 | 5/1977 | Canada . |
| 24926 | 3/1981 | European Pat. Off. ............ 556/445 |
| 1806758 | 7/1970 | Fed. Rep. of Germany . |
| 2632417 | 2/1977 | Fed. Rep. of Germany . |
| 1386876 | 3/1975 | United Kingdom . |

OTHER PUBLICATIONS

Lutz et al., *Organic Coatings and Plastic Chemistry*, vol. 38, 195–201 (1976).
Pittman, J. of Coatings Technology, 48 (617), 31-7 (1976).

*Primary Examiner*—Paul F. Shaver
*Attorney, Agent, or Firm*—Eugene C. Trautlein

[57] ABSTRACT

Pentachlorophenyl 3-(triethoxysilyl)propyl ether and its use as a mildewcide in latex paints.

1 Claim, No Drawings

PENTACHLOROPHENYL 3-(TRIETHOXYSILYL) PROPYL ETHER

CROSS-REFERENCE TO RELATED APPLICATION

Ser. No. 192,604, filed on even date herewith, discloses certain mildewcidal carbamate and ester compounds and their use in latex paints.

BACKGROUND OF THE INVENTION

1. Field of the Invention

This invention relates to pentachlorophenyl 3-(triethoxysilyl)propyl ether, a compound which has been found to exhibit mildewcidal activity. This invention also relates to latex paints containing said mildewcidal compound.

2. Description of the Prior Art

Mildewcidal-induced defacement of paint film and other organic coatings is a serious problem faced by the coatings industry, resulting in several tens of million of dollars of damage annually. Mildew growth destroys coating integrity by a series of microbial (including bacterial and fungal) degradations of paint film components. Hydroxy Ethyl Cellulose, which is often used as a binder in water-based latex paint formulations, is especially susceptible to microbial degradation, and therefore latex paints as a class are especially susceptible to mildew attack.

Although the exact mechanism of mildew growth on a paint film has not yet been determined, considerable evidence suggests that mildew growth involves a sequence of bacterial and fungal attacks in which each attack renders the paint film susceptible to the metabolic processes of the next attacking organism. For effective mildew inhibition, a mildewcide must be active against a significant number of microbial species, bacterial and fungal, and especially effective against those species which cause initial damage to the paint film.

The addition of currently known mildewcidal agents such as 2-n-octyl-4-isothiazolin-3-one ("SKANE M-8") or N-pentachlorophenylethylenediamine to paint formulations provides excellent initial antimicrobial response in various paint films. However, these agents generally provide only temporary mildew inhibitions, since they are susceptible to chemical change and deactivation while still in the paint formulation, and to further deactivation in the paint film. Under outdoor environmental exposures these agents may also be subject to leaching from the paint films. A need clearly exists to develop a means of providing extended protection of paint films against mildew attack.

One method, proposed by Pittman, *J. of Coatings Technology;* 48(617), 31–7 (1976), of extending the effective life of a mildewcidal agent involves the chemical anchoring of the mildewcidal agent to a component in the paint film, e.g., the latex polymer, thus reducing the tendency of leaching of the agent from the paint film and effectively increasing the useful lifetime of the mildewcidal agent.

Lutz et al., *Organic Coatings and Plastics Chemistry,* Vol. 38, 195–201 (1976), describes the use of methyltrimethoxysilane to reinforce various organic formulations. Dried films of such reinforced latexes gave improved solvent resistance.

Other references forming part of the background of the present invention are: U.S. Pat. No. 3,253,009, which discloses silanes and siloxanes containing a moiety (RO)Si wherein R is a halogen-substituted aryl group; U.S. Pat. No. 3,542,786, which discloses compounds such

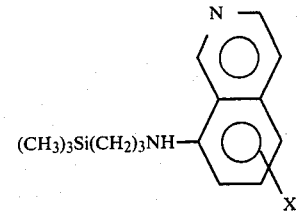

wherein X is chlorine or fluorine; U.S. Pat. No. 3,692,798 which discloses compounds of the formula

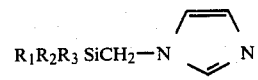

wherein each of $R_1$, $R_2$, and $R_3$ is lower alkyl or phenyl; U.S. Pat. No. 3,719,679, which discloses N-methyl- and N,N-dimethyl-3-[tris(trimethylsilyloxy)silyl]propanamine; U.S. Pat. No. 3,860,709, which discloses compounds such as that of the formula

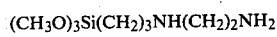

and other simpler and more complex organosilicon amines and their salts; British Pat. No. 1,386,876, which discloses organosilicon quaternary ammonium compounds; Canadian Pat. No. 1,010,782, which discloses filled polymeric matrices containing solid fillers which fillers have coated on their surfaces organosilicon quarternary ammonium compounds; West German Offenlegungsschrif No. 1,806,758, which describes various phenolic and quarternary ammonium derivatives of phenyltrichlorosilane; and West German Offenlegungsschrift No. 2,632,417, which describes various organosilicon quaternary ammonium halides.

None of the above-noted references discloses or suggests the pentachlorophenyl 3-(triethoxysilyl)propyl ether upon which the present invention is founded.

SUMMARY OF THE INVENTION

The present invention comprises a novel mildewcidal compound of the formula

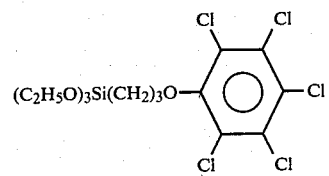

Another aspect of the present invention is the use of said noval mildewcidal compound in latex paints.

The present invention also contemplates the extension of mildew protection lifetime by the immobilization of the mildewcidal agent on the surface of inorganic fillers, e.g., silicas, such as are incorporated into most paints. Fillers so treated are a still further aspect of the present invention. The treated filler becomes the carrier for incorporation of the mildewcidal agent into a paint film. This method is an economically and technologically interesting means of achieving extended mildew inhibition. Utilization of the mildewcidal silane avoids the difficult problems encountered in the preparation of latex polymers containing chemically combined mildewcidal agents. This approach also provides considerable latitude in the use of mixtures of agents and varying concentrations to achieve synergistic and optimum effects.

DESCRIPTION OF THE PREFERRED EMBODIMENTS

The novel mildewcidal compound of the present invention has the formula

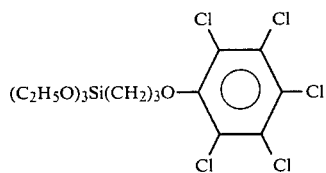

The compound of the present invention can conceptually be utilized both individually and in combination with other mildewcidal silanes, such as, for example, those disclosed in above-mentioned Ser. No. 192,604, to provide a long-lasting mildewcidal effect in latex paints. A compound, or a combination of two or more compounds, can be incorporated directly into a latex paint mixture, or it or they can be coated onto a silica filler which is then incorporated into a latex paint mixture.

The novel compound of the present invention can be prepared by the following sequence of reactions:

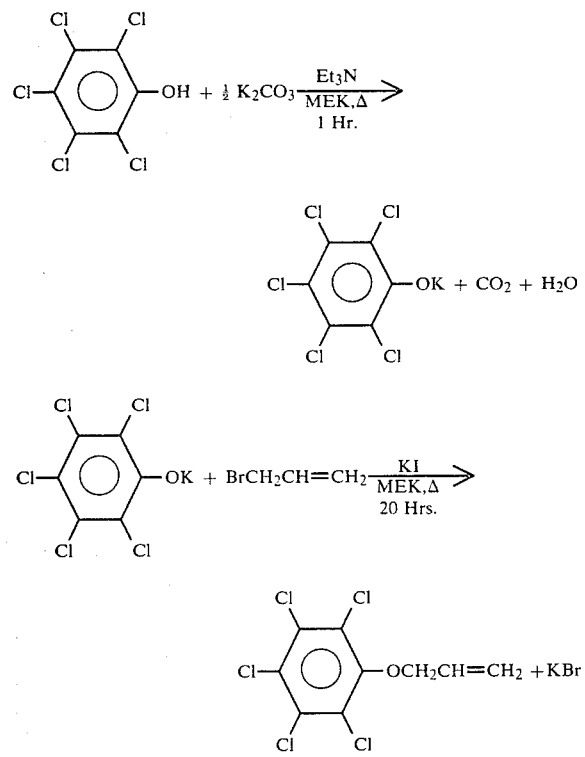

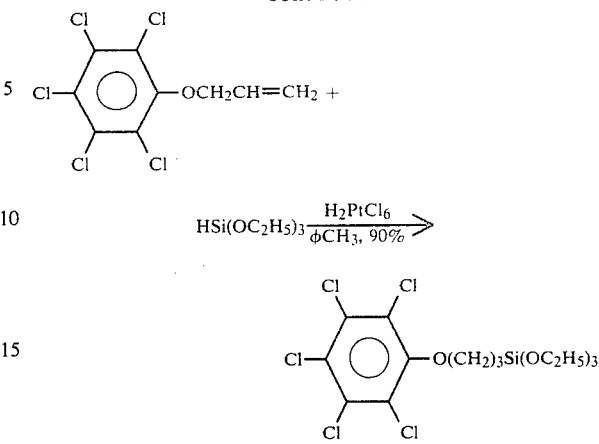

An illustrative example follows:

PREPARATIVE EXAMPLE

Into a five-hundred milliliter, one neck, round bottom flask equipped with water condenser with a nitrogen bypass were charged 41.4 parts pentachlorophenol, 22.2 parts anhydrous potassium carbonate, 2.50 parts methyl ethyl ketone as solvent, 0.1 part potassium iodide and 1.0 part triethylamine. These ingredients were heated at reflux for one hour then cooled. 51.0 parts of allyl bromide was then added and the total flask contents were subsequently heated for 20.0 hours, then cooled. The flask contents were then evaporated under reduced pressure at 60° C. to yield a solid. The solid was then extracted with 100 parts of methylene chloride and 100 parts of water. The methylene chloride layer was then extracted five times with 10% aqueous potassium carbonate followed by extraction with saturated aqueous sodium chloride solution. The methylene chloride layer was then dried over anhydrous calcium chloride and evaporated under reduced measure at 60° C. to yield a solid. The solid was then recrystallized from hot hexane to yield 38.8 parts of allylpentachlorophenyl ether of 99+% purity as shown by gas chromatography.

27.0 parts of triethoxysilane, 0.05 parts phenothiazine, and 250 ppm hexachloroplatinic acid were charged to a three-neck 100 ml round bottom flask equipped with a magnetic stirrer, thermometer, addition funnel, and water condenser with a nitrogen by-pass. 18.4 parts of allylpentachlorophenyl ether prepared as described above was then added to the dropping funnel. Flask contents were heated to 80° C. at which point the allylpentachlorophenyl ether was added dropwise keeping the exotherm below 100° C. by regulation of the addition rate. After the addition was completed (ca. 15 minutes) the total flask contents were heated at 90° C. for 30 minutes then cooled to room temperature. The flask contents were then evaporated under reduced pressure at 60° C. to yield a liquid which was subsequently vacuum distilled through a six-inch heated vigreux column at 1.0 mm Hg. 13.0 parts of 3-(pentachlorophenoxy)-propyltriethoxysilane with a boiling point of 216°–245° C. at 1.0 mm Hg was obtained. The product was identified by gas chromatography, infrared and nuclear magnetic resonance spectroscopy.

BIOLOGICAL TESTING RESULTS

A. Agar Screening Tests: Compounds

This is a general preliminary screening of the compound of the present invention for potential mildewcidal activity.

The compounds were dispersed in an agar suspension at a concentration of 500 parts per million (ppm) and subsequently inoculated with six fungal and six bacterial specimens. The fungal and bacterial species were representative species previously found to be present at various stages of mildew growth. A mildewcidal candidate has an excellent chance of providing effective mildew protection in a latex paint film, under normal weathering conditions, if it inhibits the growth of all twelve microorganisms at 500 ppm or lower in this test.

The agar to be used, CZAPEK DOX nutrient agar for fungal and bacterial growth testing, was sterilized and subsequently cooled to 55° C. At this time, the desired agar suspension was then poured into a sterilized petri-dish and allowed to harden overnight. The resulting agar plates were then inoculated with the desired bacterial suspension or fungal spore suspension (see listing below) with a multiple point inoculator. (All bacterial and fungal spore suspensions were fresh and of standardized activity.) The inoculated agar plate was allowed to air dry in a lammelar flow hood and subsequently incubated at 30° C. for 7 days. Comparison of bacterial or fungal growth was compared to appropriate control preparations.

Suspensions of the following bacteria were used:
(1) Bacillus megaterium
(2) Enterobacter aerogenes
(3) Escherichia coli
(4) Proteus vulgaris
(5) Pseudomonas aeruginosa
(6) Pseudomonas putidas Suspensions of the following fungi were used:
(1) Aspergillus niger
(2) Aureobasidium pullulons
(3) Fusarium moniliforme
(4) Penicillium citrinum
(5) Stemphylium sp.
(6) Trichoderma viride The biocidal activity was evaluated on a scale of from 0 to 6, where 0 indicates ineffectiveness and 6 indicates total inhibition. The results are reported in Table I.

TABLE I

| | Activity | |
|---|---|---|
| Compound | Fungicidal | Bactericidal |
| Pentachlorophenyl 3-(Triethoxysilyl)propyl Ether | 0 | 6 |

B. Agar Screening Tests: Treated Fillers

This is an agar screening test which was used to evaluate the antimicrobial activity of a silica compound treated with the silane of the present invention. This test is performed by dispersing the mildewcidal silane treated silica in an agar suspension and subsequent inoculation with the same six fungal and six bacterial species used in the agar screening tests of compounds reported above.

In a typical example of filler treatment, 2718.0 parts of amorphous silica filler (IMSIL A-25, Illinois Minerals, Inc.) was charged into a Patterson-Kelly Twin Shell blender equipped with a high speed intensifier bar and a dropping funnel attached to the Twin Shell blender. The silane solution was then added to the tumbling silica filler with the high speed intensifier bar on. After the silane addition was complete, the filler was tumbled with the high speed intensifier bar on for an additional 15 minutes at which time the wet filler mixture was charged to a large pan and dried for 20 minutes at 40° C. The dried silica was then stored in a tightly capped glass jar until used.

The agar to be used, CZAPEK DOX nutrient agar for fungal and bacterial growth testing, was sterilized and subsequently cooled to 55° C. At this time, the desired agar suspension was dispensed into a 25 ml polypropylene cup. The particular silane treated silica filler to be evaluated was then hand stirred into the agar suspension and the resulting agar plates were then inoculated with the desired bacterial suspension or fungal spore suspension (same as those listed in above) with a multiple point inoculator. (All bacterial and fungal spore suspensions were fresh and of standardized activity.) The inoculated agar plate was allowed to air dry in a lammelar flow hood and subsequently incubated at 30° C. for 7 days. Comparison of bacterial or fungal growth was compared to appropriate control preparations.

The biocidal activity was evaluated on a scale of from 0 to 6, where 0 indicates ineffectiveness and 6 indicates total inhibition. The results are reported in Table II.

TABLE II

| | | Activity | |
|---|---|---|---|
| Compound | Weight % of Compound on Silica | Fungicidal | Bactericidal |
| Control (Silica, No Silane Compound) | 0.0 | 0 | 0 |
| Pentachlorophenyl 3-(Triethoxysilyl)- propyl Ether | 1.2 | 6 | 5 |

C. Paint Preparation

The test paint is prepared in the following two steps:

Step 1: 136.4 parts of deionized water, 20.0 parts of ethylene glycol and 1.5 parts of a hydroxyethyl cellulose thickener were charged into a 1 liter stainless steel beaker and stirred at 625 rpm with a Cowles mixer until complete dissolution was observed. At this point, the following components were added by the indicated order of addition.

| Addition Order | Component | Parts |
|---|---|---|
| 1 | A 53% Acrylic latex (UCAR Latex 508) | 372.0 |
| 2 | Anaerobic Preservative (Proxcel CRL)* | 1.0 |
| 3 | Non-ionic Nonylphenol Ethoxylate surfactant (TERGITOL NPX) | 2.0 |
| 4 | Alkyd Resin Adhesive Promoter (Aroplaz 1271 Alkyd) | 46.0 |
| 5 | Cobalt Naphthenate (12% "NuxTra" Cobalt Drier) | 0.8 |
| 6 | Zirconium Naphthenate (12% "NuxTra" Zirconium Drier) | 0.8 |
| 7 | Isobutyl Isobutyrate (Texanol) | 10.8 |
| 8 | 2% Water Solution of Hydroxyethyl Cellulose Thickener (CELLOSIZE HEC QP-4400) | 184.0 |
| 9 | Defoamer (Nopco NXZ) | 2.6 |

*An "in-can" stabilizer

The above mixture was stirred for 10 minutes after the addition was complete. At this point, the total paint mixture was adjusted to pH 9.0 using concentrated ammonium hydroxide. The viscosity of the various test paint formulations were typically 19–105 Kreb units.

D. Long Term Paint Exposure Tests

Paints were prepared as described above in Section C but incorporating the mildewcidal agents indicated in Tables III and IV. The paints were applied to standard white pine test panels which are conventionally used for prolonged exterior exposure studies of paint films. The painted panels were then subjected to prolonged exposure studies at testing facilities (1) in Largo, Fla. and (2) in South Charleston, W. Va. The exposure conditions at the Largo Test Facility are particularly severe with respect to mildew growth. The results obtained here approximate a "worst case" situation since even many excellent mildewcidal compounds may fail after relatively short exposure trials. The testing facility at South Charleston is considerably less severe and provides a more realistic test with respect to the severity of exposure conditions. In addition to mildew protection, the South Charleston facility also evaluated the discoloration of the painted panels due to weathering. The results are reported in Tables III and IV.

TABLE III

MILDEWCIDAL SILANE EXTERIOR EXPOSURE RESULTS OBTAINED AT THE LARGO, FLORIDA TESTING FACILITY

| Mildewcide | (Conc.)[1] | Monthly Mildew Defacement Rating[2] | | | | |
|---|---|---|---|---|---|---|
| | | 2 | 3 | 4 | 5 | 6 |
| None | (0.0) | 4 | 2 | 2 | 0 | 0 |
| Skane M-8 | (0.05) | 10 | 6 | 2 | 2 | 2 |
| $C_6Cl_5OH$ | (0.06) | 2 | 2 | 0 | 0 | 0 |
| $C_6Cl_5OH$ | (0.95) | 6 | 3 | 2 | 2 | 2 |
| Pentachlorophenyl 3-(Triethoxysilyl)propyl Ether | (0.17) | 4 | 2 | 2 | 2 | 0 |

[1] Mildew concentration is based on the total weight of the paint blend. The mildewcidal silane was added to the paint via silane-treated IMSIL silica filler. The non-silylated mildewcides were added directly to the pigment grind.
[2] Paint ratings 1 = worst, 10 = best.

TABLE IV

MILDEWCIDAL SILANE EXTERIOR EXPOSURE RESULTS OBTAINED AT THE SOUTH CHARLESTON TESTING FACILITY

| Mildewcidal | (Conc.)[2] | Mildew Defacement[2] | | Discoloring[2] | |
|---|---|---|---|---|---|
| | | 6 months | 1 year | 6 months | 1 year |
| None | (0.0) | 3 | 2 | 4 | 4 |
| Skane M-8 | (0.05) | 6 | 4 | 5 | 5 |
| $C_6Cl_5OH$ | (0.06) | 3 | 3 | 6 | 6 |
| $C_6Cl_5OH$ | (0.95) | 3 | 4 | 5 | 4 |
| Pentachlorophenyl 3-(Triethoxysilyl)propyl Ether | (0.17) | 5 | 4 | 5 | 4 |

[1] Mildewcidal concentration based on the total weight of the paint blend. The mildewcidal silane was added to the paint via silane-treated IMSIL silica filler. The non-silylated mildewcides were added directly to the pigment grind.
[2] Paint ratings are 1 = worst, 10 = best.

What is claimed is:
1. The compound pentachlorophenyl 3-(triethoxysilyl)propyl ether.

* * * * *